United States Patent [19]
Hickman

[11] Patent Number: 5,828,213
[45] Date of Patent: Oct. 27, 1998

[54] METHOD AND APPARATUS FOR MAGNETICALLY SAMPLING THE UNIFORMITY OF AN ELONGATE OBJECT

[76] Inventor: Jack R. Hickman, 2120 Danny Park, Metairie, La. 70001

[21] Appl. No.: 733,944

[22] Filed: Oct. 21, 1996

[51] Int. Cl.⁶ .............. G01N 27/82; G01R 33/12
[52] U.S. Cl. .............. 324/235; 324/232; 324/242; 324/262
[58] Field of Search ............... 324/220–221, 324/228, 232, 235, 240–243, 262

[56] References Cited

U.S. PATENT DOCUMENTS

| | | |
|---|---|---|
| 2,194,229 | 3/1940 | Johnston et al. . |
| 2,555,853 | 6/1951 | Irwin .............................. 324/242 |
| 2,882,488 | 4/1959 | Price et al. . |
| 3,216,423 | 11/1965 | Blonsky et al. . |
| 4,096,437 | 6/1978 | Kitzinger et al. ........... 324/235 X |
| 4,427,940 | 1/1984 | Hirama et al. ................ 324/240 |
| 4,439,730 | 3/1984 | Kauffman ..................... 324/232 |
| 4,659,991 | 4/1987 | Weischedel .................. 324/241 |
| 4,827,215 | 5/1989 | van der Walt ................ 324/240 |
| 4,864,233 | 9/1989 | Harrison .................... 324/240 X |
| 4,929,897 | 5/1990 | Van Der Walt ............ 324/242 X |
| 5,293,117 | 3/1994 | Hwang ...................... 324/232 X |
| 5,402,066 | 3/1995 | Hickman, Jr. et al. ......... 324/242 |
| 5,414,353 | 5/1995 | Weischedel .................. 324/232 |

FOREIGN PATENT DOCUMENTS

0093566  4/1983  European Pat. Off. .

*Primary Examiner*—Gerard R. Strecker
*Attorney, Agent, or Firm*—Randall C. Brown; Rick Matos; Akin, Gump, Strauss, Hauer & Feld, L.L.P.

[57] ABSTRACT

Apparatus for performing nondestructive magnetically testing and inspection of elongate objects. The apparatus concentrically surrounds the elongate object to be tested and includes means for inducing a magnetic field in the elongate object and a partial ferrous return path for the magnetic flux emanating from a pair of magnet arrays. The partial ferrous return path is engaged with a sensor for detecting variations or flaws in the elongate object.

31 Claims, 10 Drawing Sheets

METHOD AND APPARATUS FOR MAGNETICALLY SAMPLING THE UNIFORMITY OF AN ELONGATE OBJECT

BACKGROUND OF THE INVENTION

1. Field of the Invention

The present invention relates to a device for the inspection and quality control of wire rope and cables. The device is adapted to surround a portion of a wire rope or cable to be tested. The device induces a magnetic field in the wire rope or cable and senses any deviation in the magnetic field indicating an anomaly in the wire rope or cable.

2. Description of Related Art

U.S. Pat. No. 5,402,066 discloses a device for magnetically testing an elongate object that does not include an established return path for the magnetic flux that is generated by the device and that passes through the elongate object. According to the device disclosed in this patent, flux generated by an originating magnet travels through the elongate object and into a downstream magnet and then returns to the originating magnet through the air. Changes in the metallic cross section of the elongate object are measured by sensors in the device that respond to the quantity of flux lines traveling through the elongate object. Generally, the greater the volume of material being tested that is located between the magnets, the higher the voltage produced by the sensors. Abrupt changes in the volume of the material located between the magnets, however, radiates magnetic flux in all directions proportionate to the size of the change. The flux which travels through the sensor and makes sensing possible is initiated at the elongate object and returns to the originating magnet through the path of least resistance which is through the air.

This device is highly susceptible to interference because the flux which enters the sensor from the material being tested and returns via the air gap to the originating magnet is affected by the presence of a ferrous material anywhere within the proximity of the air gap adjacent to the space between the magnet arrays or between the magnet arrays and the sensor. The presence of such a ferrous material significantly affects the return path of the magnetic flux traveling through the sensor so that an inaccurate signal is generated by the sensor.

European Patent Application No. 0,093,566 discloses a method and apparatus for non-destructive testing of magnetically permeable bodies. The apparatus disclosed in this patent application utilizes a closed magnetic field and includes a magnetic flux return path having a capacity equal to or greater than the fully saturated magnetic flux of the material being tested.

According to the device disclosed in the European Patent application, magnetic flux passes from the originating magnet array to the material being tested, travels through the material, through a second downstream magnet array and returns to the originating magnet array through a metallic magnetic flux return path. In this device, the sensor is directly connected to the metallic magnetic flux return path and the flux which enters the sensor and makes sensing possible is initiated at the material being tested and takes the path of least resistance to the originating magnet which in this case is through the metallic magnetic flux return path which connects the two magnet arrays.

There is a problem with this device in that the metallic magnetic flux return path which connects the two sets of magnets causes the sensor to measure only a portion of the variance in the material being tested. Specifically, since the sensor housing is directly connected to the metallic magnetic flux return path the south pole of the magnet which emitted the flux is extended to a point on the sensor an equal distance from the north pole of the same magnet which emitted the flux. This arrangement limits the radiation of flux caused by changes in the metallic area of the material being tested because the sensor is located on one end of the magnet which emitted the flux rather than in the air gap between the south and north poles. The greatest deviation of flux due to a deviation in the material being tested is in the center of the space between the south and north poles. Essentially, the flux within the return path between the two magnet sources negates a portion of the return flux of the sensor. Therefore, the sensor cannot fully detect the magnetic flux deviations.

A need exists, therefore, for a method and apparatus for magnetically testing elongate objects that is not subject to interference from metallic objects placed in close proximity to the device and at the same time permits accurate detection of magnetic flux deviations in a test sample.

SUMMARY OF THE INVENTION

The apparatus of the present invention overcomes the above-mentioned disadvantages and drawbacks which are characteristic of the related art. The apparatus of the present invention includes a metallic magnetic flux return path that has the capacity to carry the maximum allowable magnetic flux deviance generated by a fault in the material being tested. The magnetic return path of the sensor only is established by a metallic material extending between the null points of a first magnetic array and a second magnetic array, respectively, and being connected to the sensor while keeping the sensor housing out of the return path of the magnetic field generated by the first and second magnet arrays, which magnetic field saturates the material being tested.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings.

DESCRIPTION OF THE PREFERRED EMBODIMENTS

Figure 1:
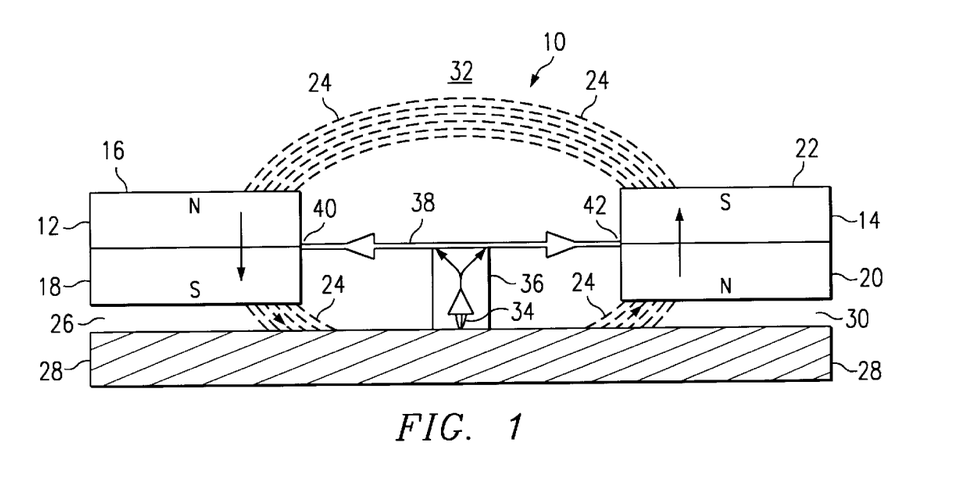
FIG. 1 is a schematic drawing of a typical section of the magnetic flux generated by the magnets in the apparatus of the present invention and passing through the material to be tested.

Referring now to the drawings, and particularly to FIG. 1, a schematic drawing of a preferred embodiment of the apparatus for magnetically testing elongate objects of the present invention is shown and generally designated by the reference numeral 10. The device includes a first magnet array 12 and a second magnet array 14. Each magnet in the first magnet array has a north pole 16 and a south pole 18. Each magnet in the second magnet array 14 has a north pole 20 and a south pole 22. The magnetic flux 24 generated by the first magnet array 12 emanates from the south pole 18 and jumps air gap 26. The magnetic flux 24 then passes through the material to be tested 28. All or a portion of the magnetic flux 24 jumps air gap 30 and enters the north pole 20 of the second magnet array 14. The magnetic flux 24 then emanates through the north pole 20 to the south pole 22 and jumps air gap 32 so as to return to the north pole 16 of the first magnet array 12.

As the magnetic flux 24 passes through the material to be tested 28 any abrupt changes in the metallic cross-section results in radiation of the magnetic flux 24 in all directions proportionate to the size of the change. A portion of the radiated magnetic flux 34 caused by the abrupt change in the metallic cross-section of the material to be tested 28 enters sensor 36. The sensor 36 responds to the quantity of flux lines radiating from the material to be tested 28. The radiated magnetic flux 34 passes through the sensor 36 and returns to either the first magnet array 12 or the second magnet array 14 through a metallic magnetic flux return path 38 that is engaged with the sensor 36 and the theoretic null points 40 and 42 of the first magnet array 12 and the second magnet array 14, respectively. While the metallic magnetic flux return path is engaged with the sensor 36, the sensor housing is sited to avoid interfering with the return path of the magnetic flux 24. The metallic magnetic flux return path 38 has a magnetic flux capacity equal to the maximum allowable magnetic deviance of the material to be tested 28. If the maximum allowable magnetic deviance for the material to be tested 28 is reached, it is unnecessary to detect a higher magnetic deviance because the material to be tested 28 will be determined to have failed the test. The magnetic flux capacity of the metallic magnetic flux return path 38 only has to be large enough to carry the flux generated by the maximum allowable deviance for the material to be tested. Thus, the apparatus 10 of the present invention includes a partial magnetic return path 38 for the magnetic flux 24. In other words, the magnetic flux return path 28, preferably, has a maximum capacity to return to the first magnet array 12 and the second magnet array 14 magnetic flux that is less than or equal to the maximum allowable flux deviance for the material to be tested 28.

Figure 2:
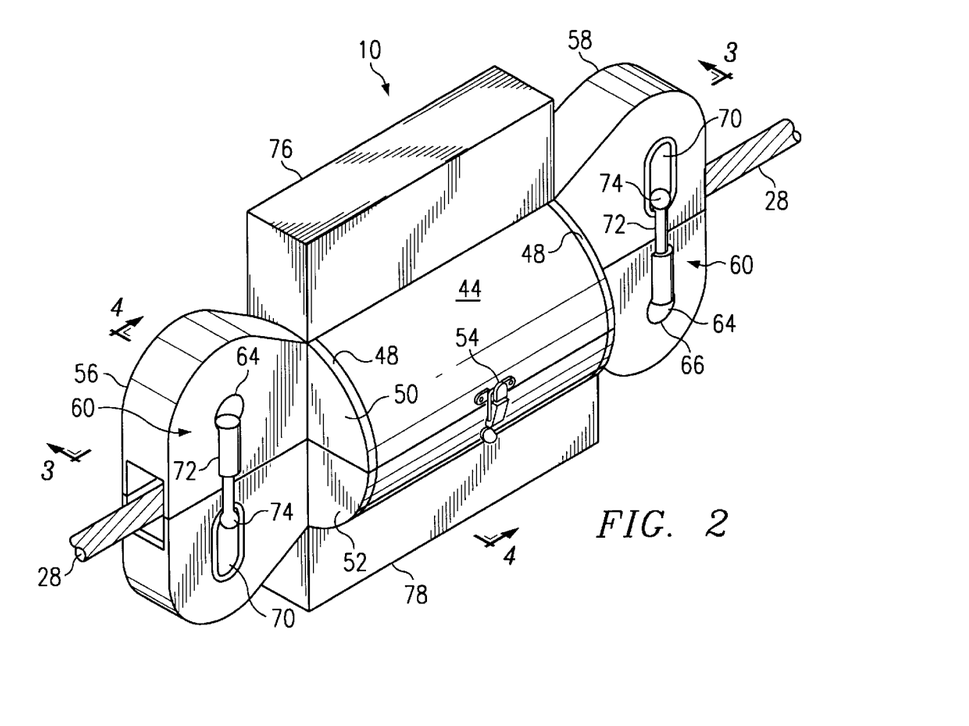
FIG. 2 is a perspective view of the apparatus for magnetically testing elongate objects of the present invention.

Referring now to FIG. 2, a preferred embodiment of the apparatus of the present invention is generally indicated at 10. The apparatus is adapted to concentrically surround a metal rope, wire, pipe, tubing, cable, ingot or stock 28 to be tested for anomalies in its cross-sectional profile. As used herein, the term cable shall refer to any type of rope, wire, pipe, tubing, cable, metal stock, or the like, made of metallic material.

Figure 3:
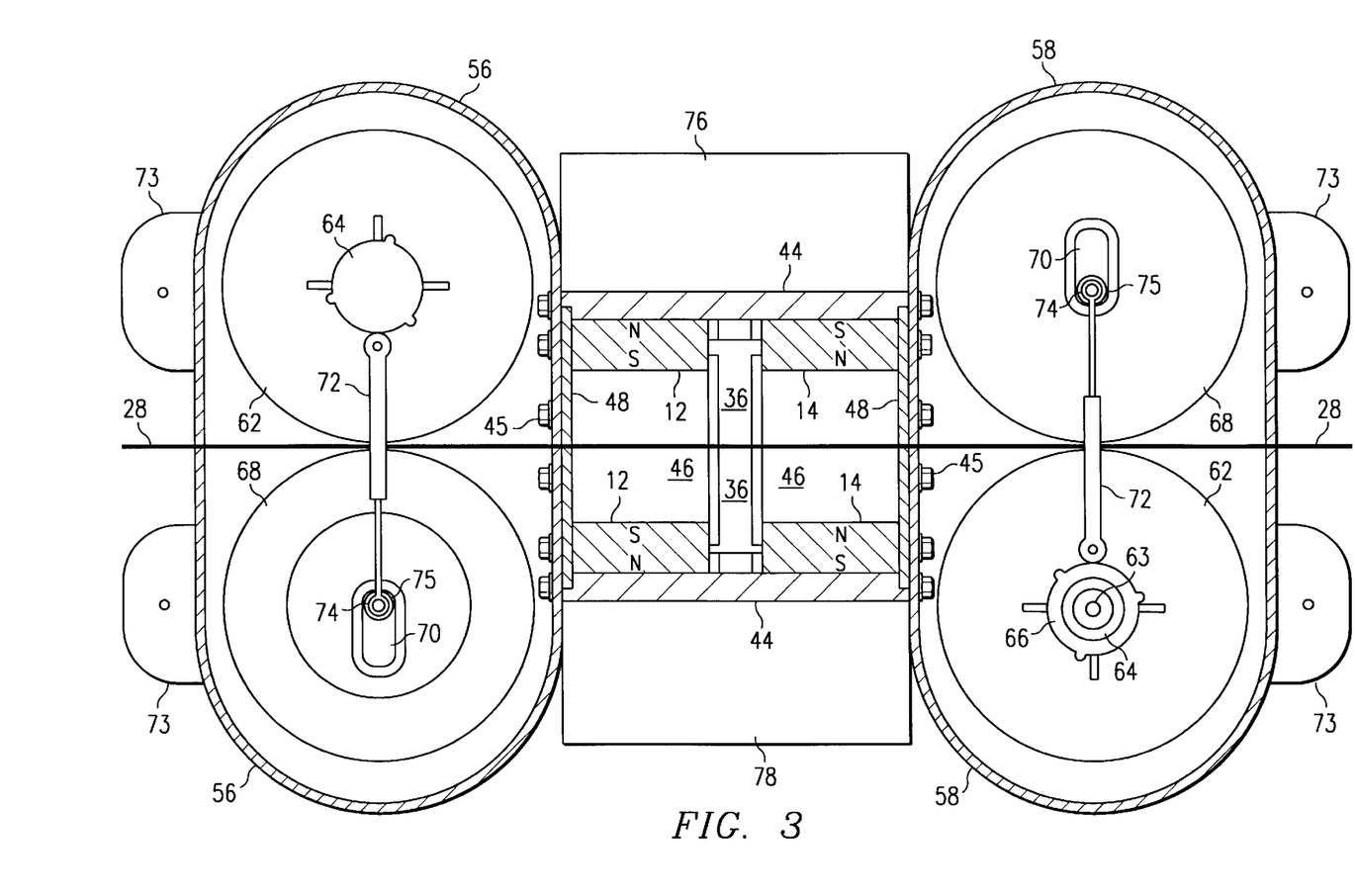
FIG. 3 is a partial section taken along line 3—3 of FIG. 2 and a partial schematic drawing of the apparatus for magnetically testing elongate objects of the present invention in which the shock absorbers of the wheel assemblies are shown schematically while the remainder of the apparatus is shown in section.

As shown in FIGS. 2 and 3, the apparatus for magnetically testing elongate objects includes a housing 44 for containing the first magnet array 12, the second magnet array 14 and the sensor 36. The cable 28 is centrally located within a central bore 46 which runs the entire length of the apparatus for magnetically testing elongate objects 10 from the first magnet array 12, through the sensing device 36 and through the second magnet array 14. The housing 44 has end caps 48 at either end thereof.

The housing 44 has two halves 50 and 52 which are hinged on one side and held together or allowed to open by a latching mechanism 54 on the opposite side. This structure allows the apparatus of the present invention to be placed over the material to be tested and to concentrically surround it.

The apparatus for magnetically testing elongate objects includes a first guide wheel housing 56 and a second guide wheel housing 58. The guide wheel housings 56 and 58 are attached to the housing 44 by fastening devices such as bolts 45.

The guide wheel assemblies 60, as shown more clearly in FIG. 3, each include a fixed guide wheel 62, one of which also includes an encoder 66, the purpose of which will be discussed below.

The guide wheel assemblies 60 also include a movable guide wheel 68 that is adapted to move in a downward-upward relationship with respect to the fixed guide wheel 62. The movable guide wheel 68 is adapted to maintain the linear position of all the guide wheels 62 and 68 in the direction of the material to be tested. The movable guide wheel 68 is adapted to move or slide in a downward-upward relationship with respect to the fixed guide wheel 62 by means of a slot 70 disposed in the housing 44. In a preferred embodiment of the present invention, the guide wheels 62 and 68 are made of nylon or a similar material well known to those of ordinary skill in the art.

The fixed guide wheel 62 provides a base for the mounting of a shock arresting device 72 which absorbs the movement and shock from the movable guide wheel 68 when an immediate surface change in the material to be tested 28 occurs. Preferably, the housings also provide means 73 to attach the apparatus to a cable or to mount the apparatus.

Figure 6A:
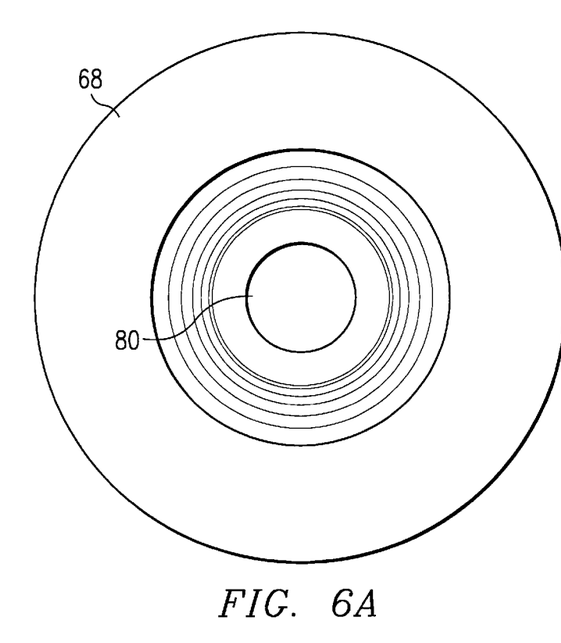
FIG. 6A is a front plan view of a second guide wheel for the apparatus for magnetically testing elongate objects of the present invention.
Figure 6B:
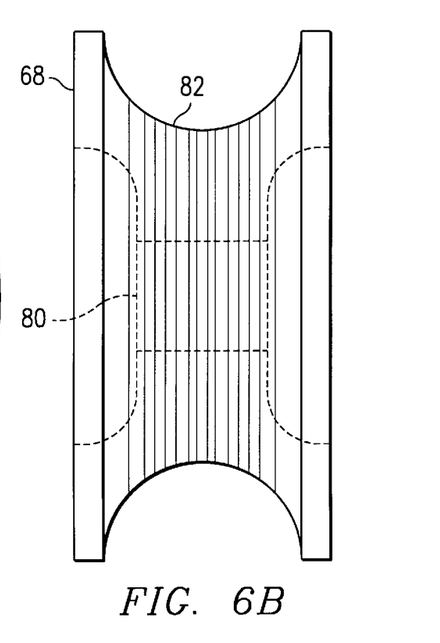
FIG. 6B is a side plan view of a second guide wheel for the apparatus for magnetically testing elongate objects of the present invention.

As shown in FIG. 6B, the outer circumference of the guide wheels 68 also include a groove 82 to provide minimal guidance to the material being tested 28.

Referring again to FIG. 3, the electronics and backup battery supplies can either be located in enclosures 76 and 78 which are directly attached to the apparatus of the present invention or remotely located at a distance from the testing device. Preferably, if the device is located remotely at a distance of greater than fifty feet from the electronics an additional digital electronic assembly is added to the device of the present invention to transfer the data from the sensors 36 to the electronic processor assembly.

Figure 4:
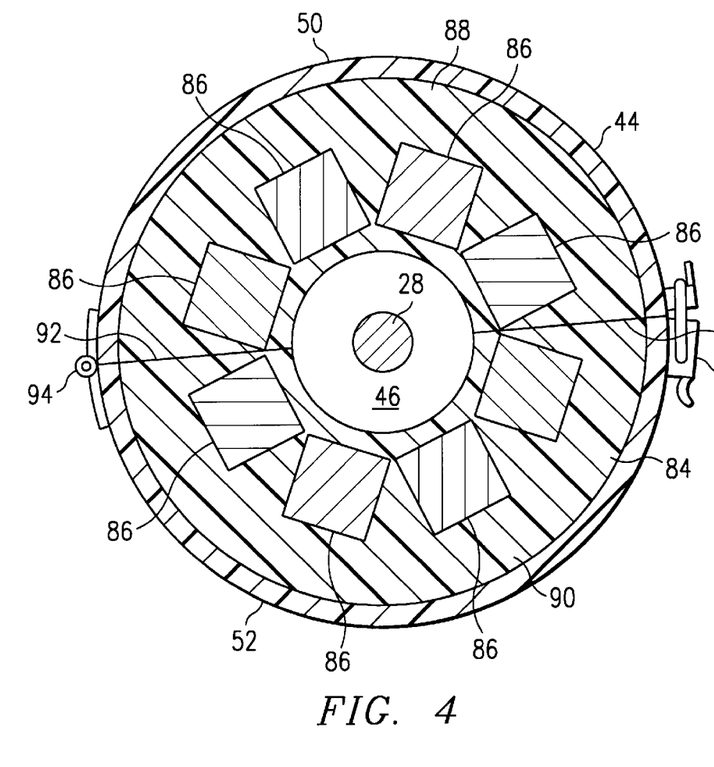
FIG. 4 is a section taken along line 4—4 of FIG. 2 of the apparatus for magnetically testing elongate objects of the present invention.
Figure 5A:
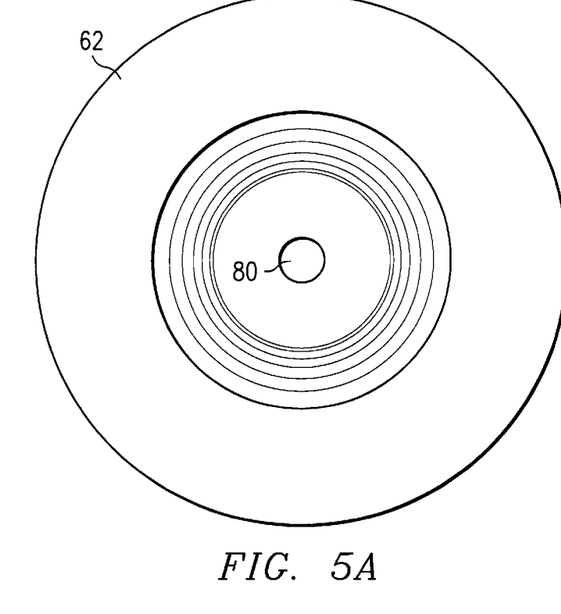
FIG. 5A is a front plan view of a first guide wheel for the apparatus for magnetically testing elongate objects of the present invention.
Figure 5B:
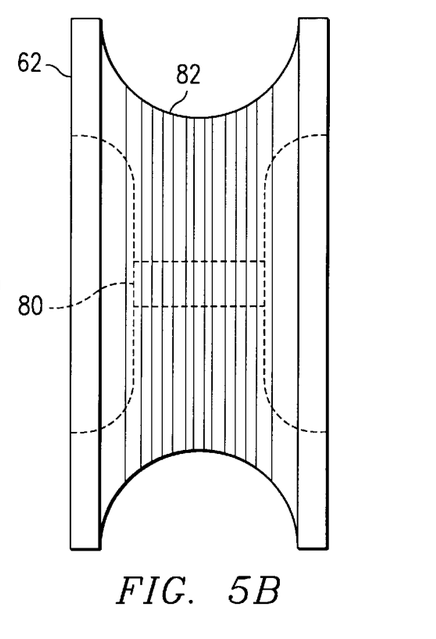
FIG. 5B is a side plan view of a first guide wheel for the apparatus for magnetically testing elongate objects of the present invention.

As shown in FIG. 4 the apparatus for magnetically testing elongate objects of the present invention includes an inner housing 84 concentrically disposed within the housing 44. A plurality of permanent magnets 86 are located within cavities in the inner housing 84 to form a segmented cylinder spaced apart from and surrounding the material to be tested 28 with all of the magnets 86 being disposed such that the same pole of each of the magnets 86 is facing inward toward the material to be tested 28. The inner housing 84 preferably comprises a nonconductive plastic resin such as polyethylene or a similar material well known to those of ordinary skill in the art. Those of ordinary skill in the art will recognize that other nonconductive materials could be used to form the inner housing 84. Those of ordinary skill in the art will also recognize that the permanent magnets 86 can be formed of any magnetic material capable of generating sufficient flux to fully saturate the material to be tested 28. Such alternative materials include ferrite and neodymium.

Although not shown in the drawings, the second magnet array 14 is similar to the first array, and also includes an arrangement of the inner housing 84 and an identical number of permanent magnets 86, it being understood that the magnets within the second magnet array 14 are also disposed so that the same pole of each of the magnets 86 is facing inward toward the material to be tested 28, that pole however being the opposite pole as the pole facing inward within the first magnet array 12.

As discussed above, the housing 44 is split into a first housing half 50 and a second housing half 52. As shown in FIG. 4, the inner housing 84 likewise is split into a first inner housing half 88 and a second inner housing half 90 by means of a medial slit 92. In a similar manner, all corresponding parts of the second magnet array 14 and the sensor 36 are split in half by means of a medial slit 92. The split halves of the housing 44 are maintained in facing relationship by a hinge 94 and the latching mechanism 54.

As shown in FIGS. 5A, 5B, 6A and 6B, in a preferred embodiment of the present invention, two types of guide wheels are utilized in the apparatus. As shown in FIGS 2 and 3, the guide wheels 62 shown in FIGS. 5A and 5B include a bore 80 (shown in phantom in FIG. 5B) that is press fit on shaft 63, which shaft is supported by reduced friction bearings 64. Preferably, the fixed guide wheel is fixed to the shaft 63. The reduced friction bearings 64 are located in recesses in the housing 44. The outer circumference of the guide wheels 62 include a groove 82 to provide minimal guidance to the material being tested 28.

As shown in FIGS. 2,3, 6A and 6B, the movable guide wheels 68 also include a bore 80 to accept reduced friction bearings 75 through which a support shaft 74 is press fitted. The shafts 74 protrudes through the slots 70 of the wheel housings 56 and 58 and are supported by shock arresting devices 72 attached to the wheel housings 56 and 58. Those of ordinary skill in the art will recognize that any of the well known shock arresting devices 72 may be used in place of the shock absorber type device shown in FIG. 2.

Figure 7:
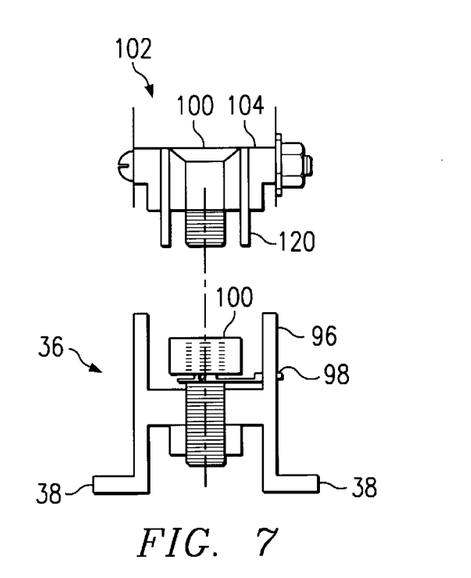
FIG. 7 is a schematic drawing of an armature adapter for the apparatus for magnetically testing elongate objects of the present invention.

As previously shown in FIG. 3, sensors 36 are engaged with the first magnet array 12 and the second magnet array 14 at the theoretical null point of each of the permanent magnets. FIG. 7 shows a detailed view of the sensor assembly 36. The sensor assemblies 36 include a sensor housing 96, an even number of digital L-Hall magnetic sensor devices 98, an armature 100 and the metallic magnetic flux return paths 38 which are engaged with the permanent magnets 86. The sensor assemblies are placed in a circumferential array between the innermost portion of the first and second magnet arrays 12 and 14, are located on the same plane as one another and placed precisely in the center of the space between the first and second magnet arrays 12 and 14. Those of ordinary skill in the art will recognize that the number of sensor assemblies 36 in the array is limited only by the space available. This array of sensors 36 enables the definition of a local fault in the material to be tested 28 as opposed to a loss of metallic area.

As noted above, each of the L-Hall sensors 98 is contained within the sensor housing 96 and is located between the housing 96 and the armature 100. The sensor housing 96 is designed so as to shield the L-Hall sensor 98 from the first and second magnet arrays 12 and 14 on either side of the L-Hall sensor 98 and also provide the return path 38 for the magnetic flux 24, which is emitted from the material to be tested 28 and passes through the L-Hall sensor 98, to a magnetic null point which is located in each permanent magnet 86 of the first and second magnet arrays 12 and 14 approximately in the center of one side of the magnet and perpendicular to the direction of charge of each of the permanent magnets 86 which make up the first and second magnet arrays 12 and 14. In so doing, the shield provided by the sensor housing acts like a hood in isolating the pure signal of a small portion of the material to be tested, thereby avoiding magnetic flux from other portions of the test material from reaching the sensor.

The housing 96 and armature 100 containing each L-Hall device 98 is separated from adjacent housings, armatures and L-Hall assemblies by an air gap that is greater than the distance between the armature 100 and sensor housing 96 and is occupied by the L-Hall device 98 and any distance between the sensor housing 96 and the point at which it connects to the null point on each of the first and second magnet arrays 12 and 14.

The output of each L-Hall sensor 98 is monitored independently. The output of all L-Hall sensors 98 is used to calculate the precise location of a magnetic anomaly by mathematical triangulation calculations. Therefore, if two sets of sensor assemblies 36 were located next to each other within the space between the first and second magnet arrays 12 and 14, enough data could be collected to create a three dimensional computer image of the magnetic field.

In a preferred embodiment, to enable the device to generate premium data from the local fault (LF) L-Hall sensors 98 when testing material diameters at a distance greater that 0.5 inches away from the LF sensor assembly 36, it is preferred to utilize an adapter 102 as is also shown in FIG. 7 to allow the sensor to sample flux closer to the material. The adapter 102 effectively extends the side magnetic shields 104 on the sensor housings 96 and the armature 100 to a point where the shields 104 and armature 100 are a maximum of 0.5 inches away from the material to be tested, but are not directly connected to the material. An insulator 120 maintains the necessary spacing between the armature 100 and the sensor housing 96 which as explained above has to be greater than the distance between the armature 100 and the sensor housing 96 and is occupied by the L-Hall device 98. In a preferred embodiment adapters 102 of various sizes may be provided to enable the testing of a full range of sizes of material.

Figure 8:
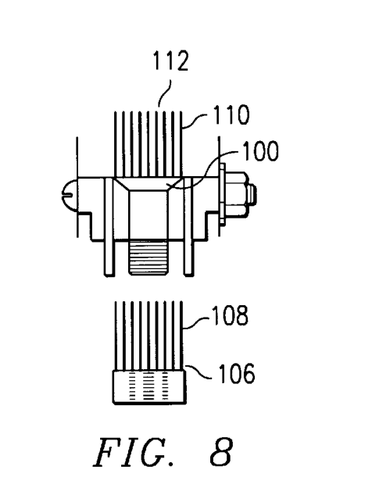
FIG. 8 is a schematic drawing of an alternate armature and an alternate adapter for the apparatus for magnetically testing elongate objects of the present invention.

In an alternate embodiment shown in FIG. 8 an alternate armature 106 is shown which is suitable for testing situations where deviations of the air gaps between the material being tested 28 and the sensor armature 106 may exceed +/−0.5 inches. The armatures 106 have small diameter flexible ferrous wires 108 protruding from their ferrous base to a point very close but not touching the material being tested 28. In this configuration the magnetic flux deviations created by anomalies in the material being tested 28 are attracted by the opposite polarity of the wires and move through the sensor 36, returning to the radiating magnet array 12.

FIG. 8 also shows an alternate embodiment of an adapter 110 having flexible ferrous wires 112 that may be attached to the armature 100 for the same reasons as noted above with respect to the alternate armature 106.

Figure 9:
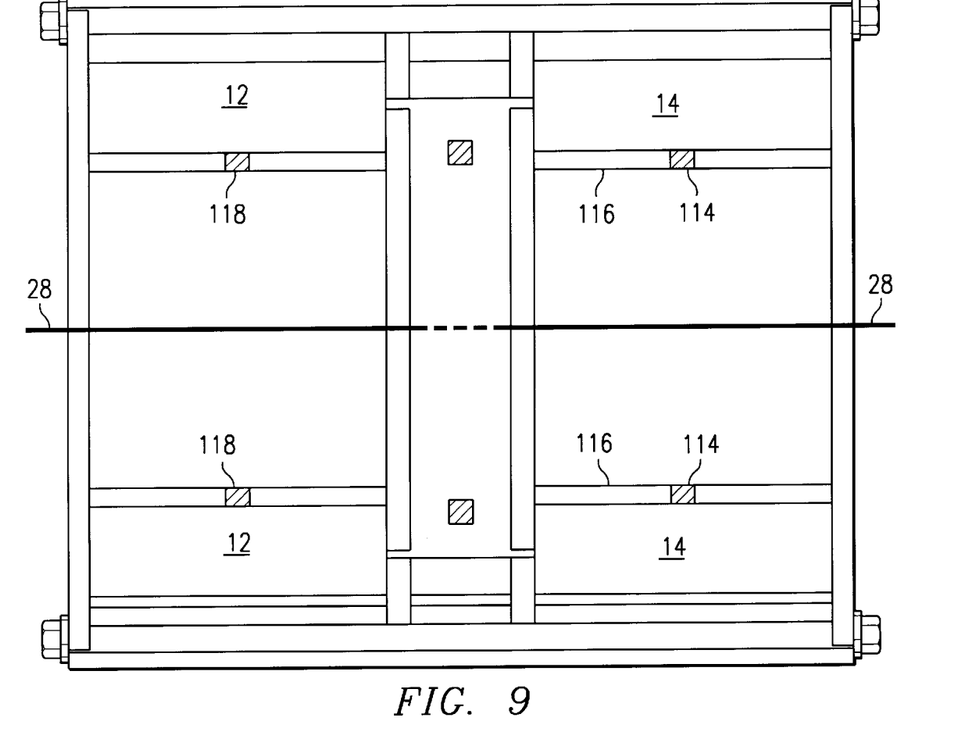
FIG. 9 is a schematic drawing of a second array of digital L-Hall sensors for the apparatus for magnetically testing elongate objects of the present invention.

FIG. 9 shows a second array of digital L-Hall sensors 114 that are located in the second magnet array 14 directly in the center of the magnetic return path at the point where the flux lines from the material being tested 28 travel through the air gap between the material being tested 28 and the innermost surface 116 of the second magnet array 14. The output of the second array of L-Hall sensors 114 is used for two purposes. First, they are used to measure the Loss of Metallic Area (LMA). Second they are used to calculate the exact location of the material being tested 28 within the bore 46 of the second magnet array 14. Those of ordinary skill in the art will recognize that a similar array 118 could be used in the first magnet array to improve the accuracy of the measuring device.

The process of determining the exact location of the material being tested 28 within the magnetic field is a tremendous improvement in the art. The data gained by these sensors and applied to the local fault data improves the accuracy of the results of a test by as much as fifty percent.

As shown in Fig. 3, an optical encoder 66 which is directly attached to the shaft of one of the two guide wheels 62 used to guide the material being tested 28 through the two magnet arrays 12 and 14. The optical encoder 66 measures the distance the material to be tested 28 has moved from the point of the beginning of a test. The digital output of the optical encoder 66 is used to determine the precise location of the material being tested 28 relative to the starting point of the test and to trigger the capture of data by all other sensors.

Figure 10:
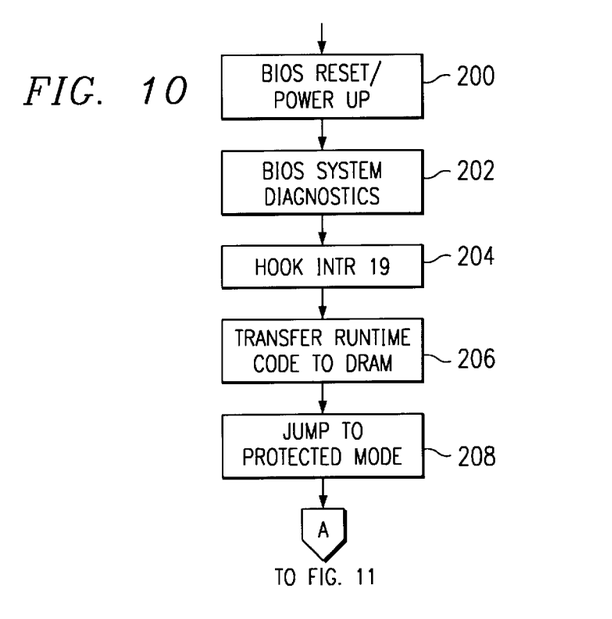
FIG. 10 is a flow chart illustrating the program logic for the embedded code power up/reset.
Figure 11:
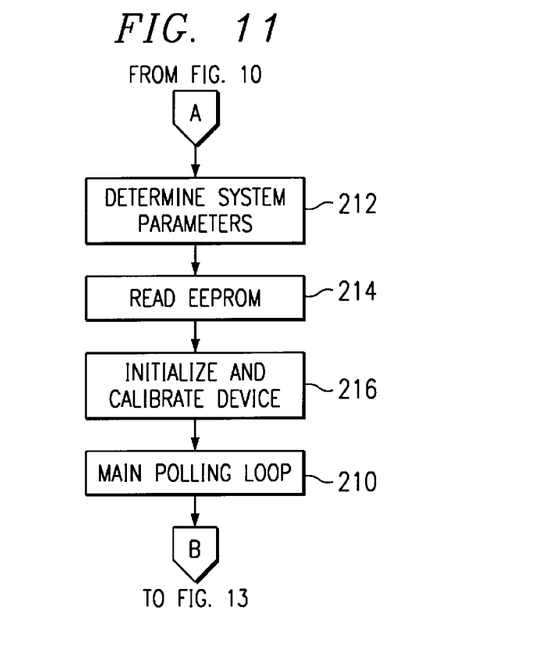
FIG. 11 is a flow chart illustrating the program logic for the embedded code main polling loop start up.
Figure 12:
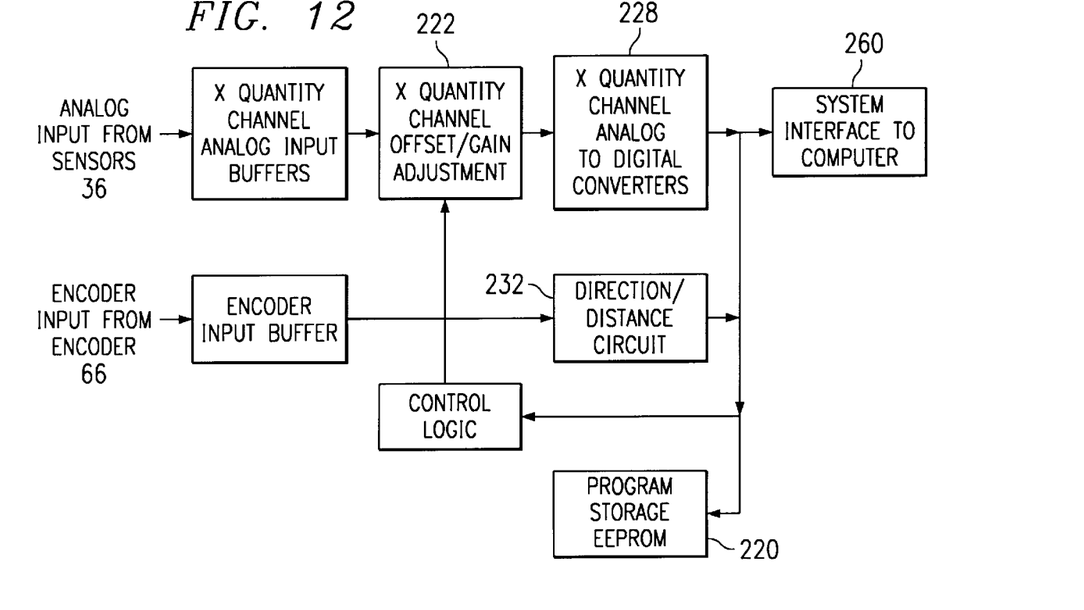
FIG. 12 is an schematic of the electronics for sampling data from the apparatus for magnetically testing elongate objects of the present invention and providing such data to a computer interface.

FIG. 10 is a drawing of the computer initialization embedded code or program and implements the logic of the microcontroller. When power is initially supplied to the computer circuitry or interrupted and then resumed as shown in block 200, the processor is instructed by the embedded code Bios System Diagnostics 202 to test all of the communications between the computer and all external devices such as sensor circuitry interface, I/O devices and memory devices. If any of the external devices do not respond properly, the processor notifies the operator of such condition via an alarm signal. The program utilizes interrupt (19) 204 to facilitate the transfer of the Runtime Code to DRAM 206. The computer is instructed to operate in protected mode 208, whereas, the RAM is utilized in such a fashion as to facilitate maximum speed of data storage in RAM. The program then moves to FIG. 11 and instructs the computer to utilize the embedded code main polling loop 210 by first Determining the System Parameters 212, then Reading 214 the EEPROM 220 (see FIG. 12). It reads the last set of instructions placed in memory on the EEPROM 220 and Initializes and Calibrates 216 all of the Offset/Gain Adjustment 222 devices on it. The Embedded Code Main Polling Loop 210 is then fully functional.

Figures 13, 14:
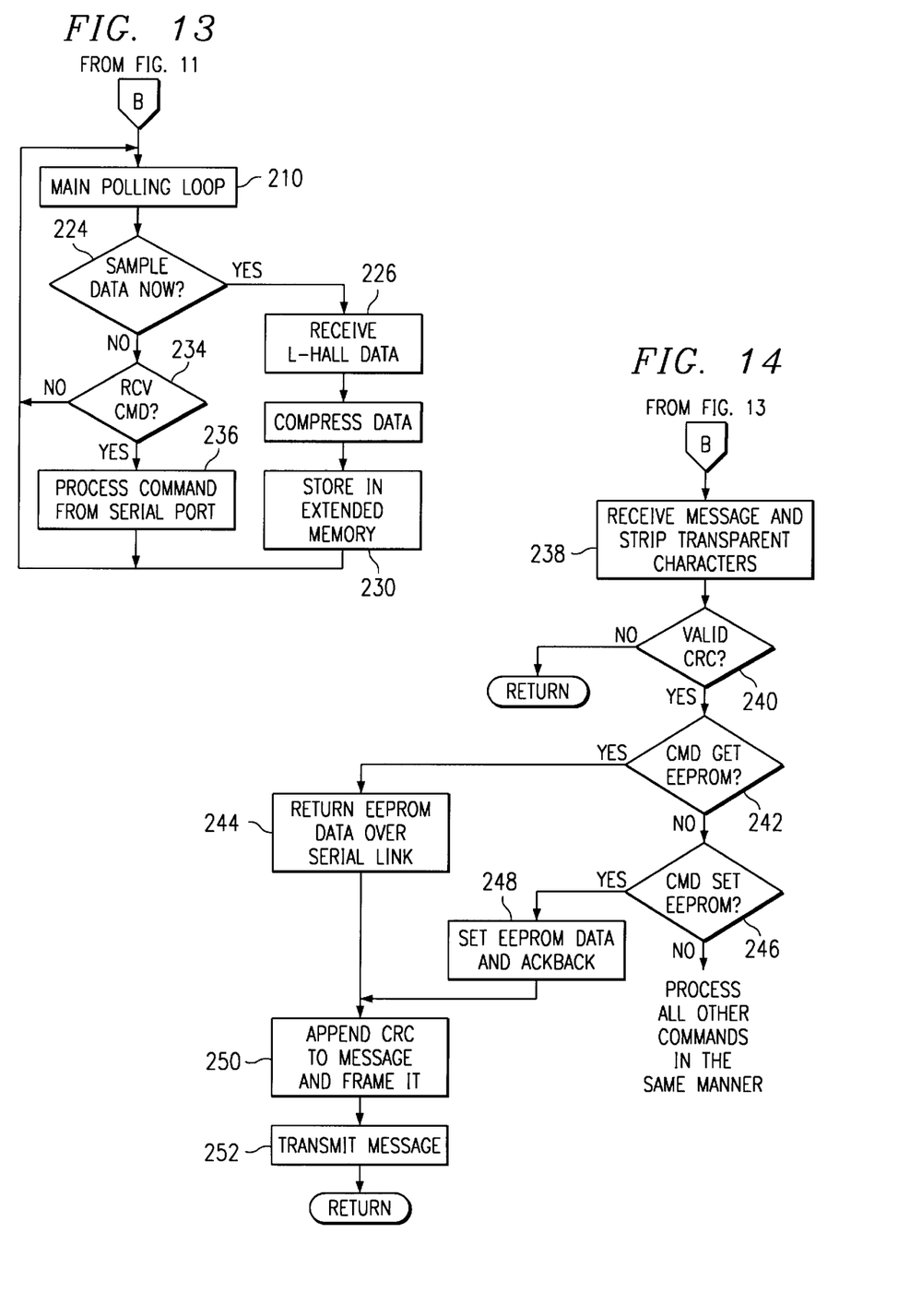
FIG. 13 is a flow chart illustrating the program logic for the embedded code polling loop.
FIG. 14 is a flow chart illustrating the program logic for the embedded code command processing loop.

As shown in FIG. 13, the Embedded Code Main Polling Loop 210 is then queried 224 whether to sample data. If (yes), L-Hall Data is received 226 from sensors 36 (see FIG. 7) via an Optical Encoder 66 (see FIG. 3) the program retrieves the data from each of the Analog to Digital Converters 228 (FIG. 12) in a predetermined sequence and stores it in the extended memory portion of RAM 230. The Main Polling Loop 210 then continues where it began. If (no) then an Optical Encoder signal 232 has not been received. The loop then checks 234 the Serial I/O Port for receipt of process commands 236. If (no) the Main Polling Loop 210 continues where it began.

If (yes) Process Commands are received from the Serial I/O Port by the Main Polling Loop 210 and sent to the Command Processing Section of the program (see FIG. 14) and all transparent characters are stripped 238 from the process commands. The program then checks the validity 240 of the received command by its leading and ending characters. If (no) the process commands 236 are rejected and the program returns to the beginning of the Main Polling Loop 210. If (yes) the program establishes communication 242 with the EEProm 220 and Returns the Data stored in it to the serial port 244, it also modifies the EEProm Data 246 as instructed and acknowledges the data 248 it received to the sender. It Appends 250 the data being sent and frames it in blocks as it Transmits 252 it to the serial port. It should be noted that a parallel port can be utilized in the same fashion and for the same purposes as the serial port is herein specified. The Command Processing Code 236 then returns to where it began. All other commands are processed in the same manner.

The apparatus of the present invention may also be operated according to a remote display computer configuration program. Such a program is a combination of several independent programs when put together form one master program.

The program configuration can be read from the hard disk of a computer according to techniques well known to those of ordinary skill in the art. The computer is typically kept separate and apart from the testing device of the present invention, but is sometimes connected to the said device by a communication cable, is used to display the data collected within the formats specified, as per the user's request. Also the system can be interfaced to a conventional computer 260 to download the data stored in the EEPROM 220. Alternatively, RAM may be used for data storage.

Figure 15:
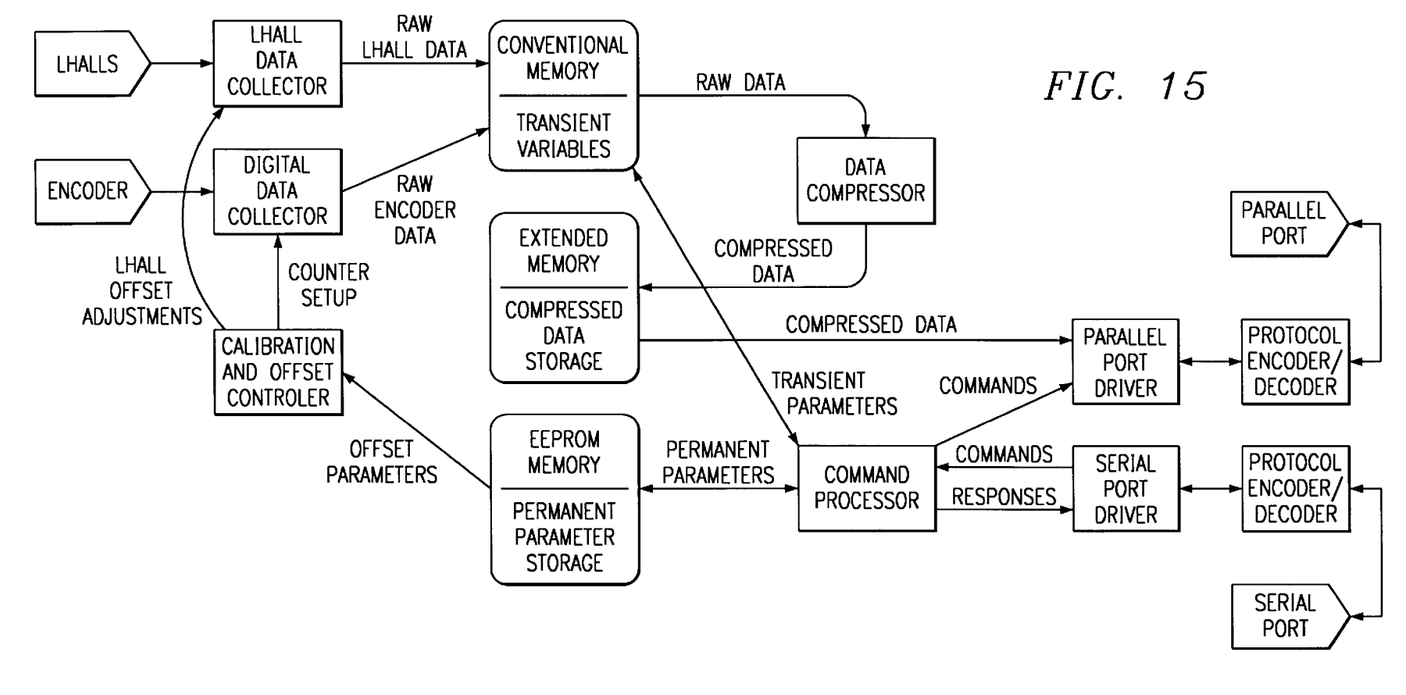
FIG. 15 is an overview flow chart illustrating the program logic for the apparatus for magnetically testing elongate objects of the present invention.

An overview flow chart of the program logic of the apparatus for testing elongate objects according to the present invention is shown in FIG. 15. Those of ordinary skill in the art will understand that the overview flow chart incorporates the individual flow charts of FIGS. 10–11 and 13–14.

Figure 16:
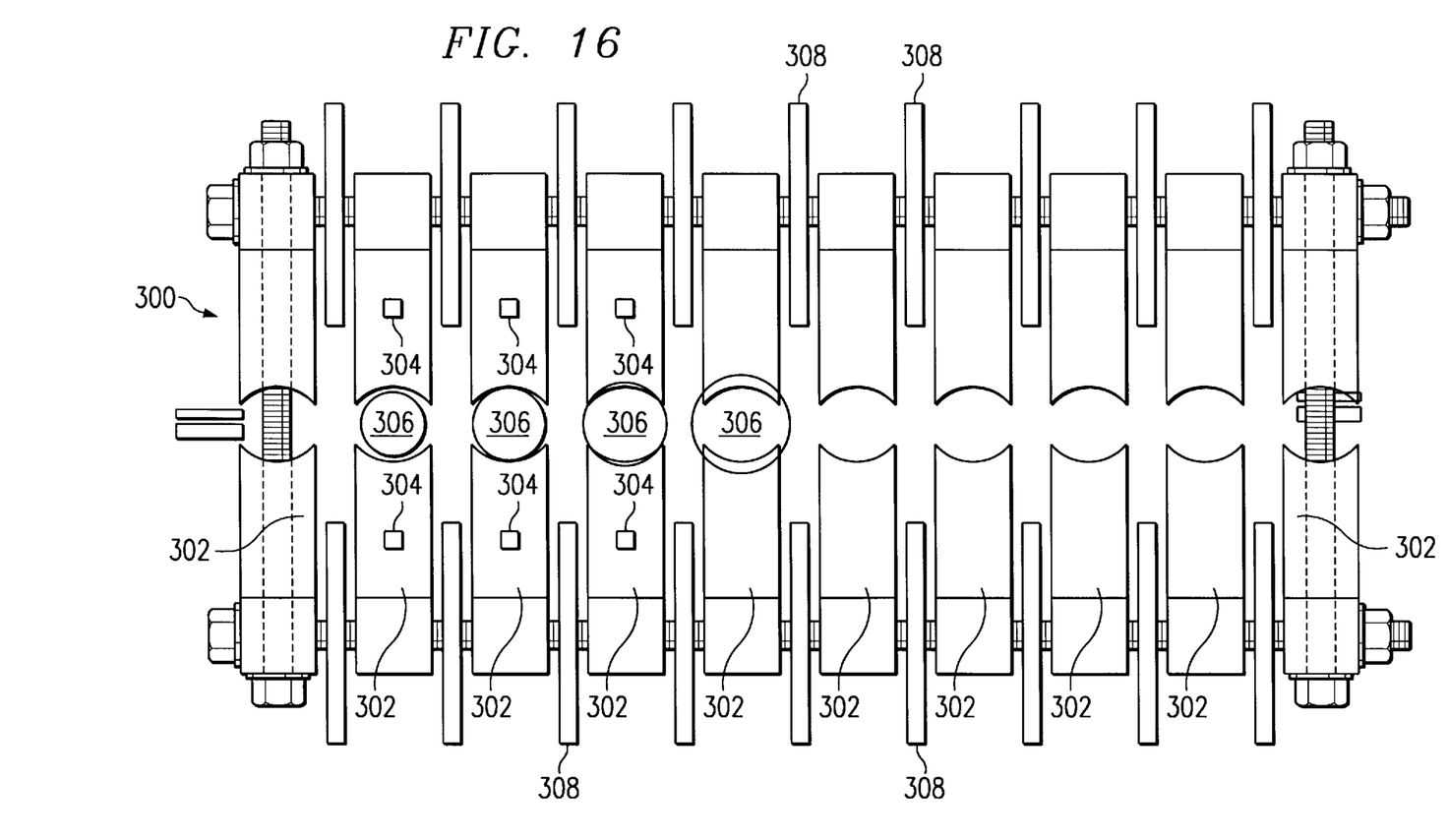
FIG. 16 is a side plan view of an alternate embodiment of the present invention adapted to magnetically test a plurality of elongate objects.
Figure 17:
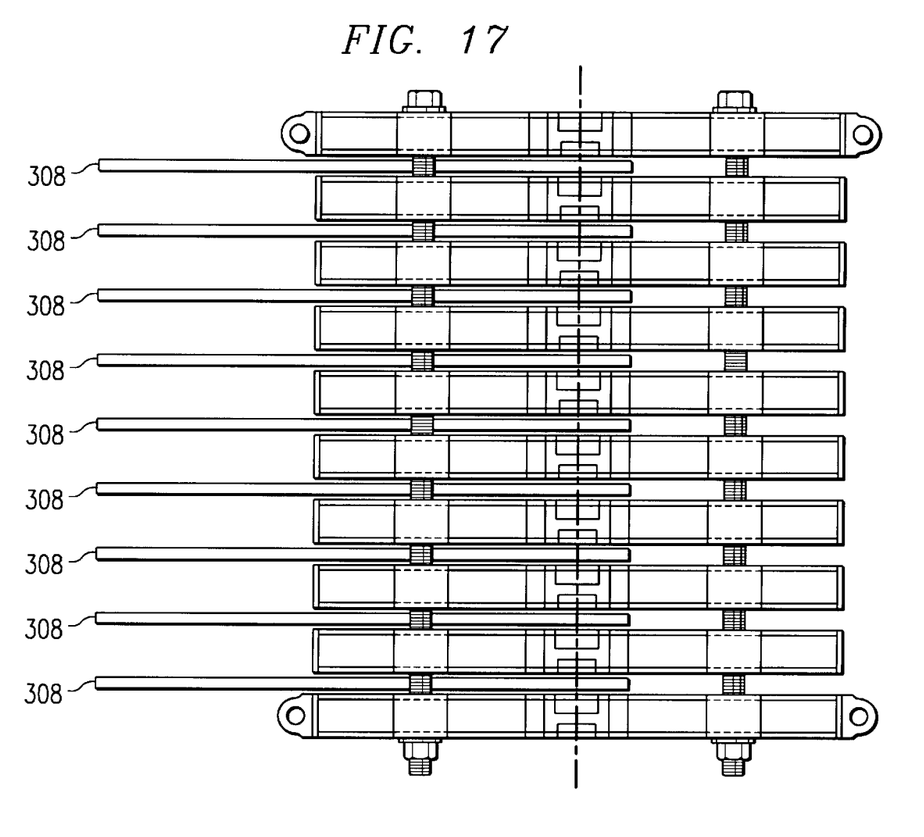
FIG. 17 is a top plan view of an alternative embodiment of the present invention adapted to magnetically test a plurality of elongate objects.

An alternate embodiment of the apparatus for testing elongate object according to the present invention is shown in FIGS. 16 and 17. This embodiment of the invention is especially well suited for application in the cabling of elevators in which there are multiple parallel and closely spaced cables. Specifically, FIG. 16 is a side view of the alternate embodiment 300 of the present invention. As shown schematically in FIG. 16, the alternate embodiment 300 includes closely spaced magnet arrays 302 and sensors 304. Elevator cables 306 pass through the gap between the magnet arrays. The sensors 304 and magnet arrays 302 operate in the same manner as described above with respect to the embodiment of the present invention shown in FIGS. 1–9. Non-magnetic spacers 308 are disposed between adjacent magnet arrays to prevent magnetic interference therebetween. FIG. 17 is a top view of the alternate embodiment shown in FIG. 16. In the top view shown, the elevator cables 306 run parallel to the spacers 308.

While preferred embodiments of the invention have been shown and described, it will be understood by persons skilled in the art that various changes and modifications may be made without departing from the spirit and scope of the invention which is defined by the following claims.

What is claimed is:

1. Apparatus for magnetically sampling uniformity of an elongate object, comprising:
   a housing having means for receiving said object;
   first and second magnet means disposed in said housing forming a magnetic field therebetween for passing magnetic flux through said object, said first and second magnet means respectively comprising a plurality of circumferentially disposed magnets approximating a cylindrical magnetic coil having a central cavity for receiving said object, wherein said cavities are longitudinally aligned, and
   sensing means for sensing variations in said magnetic flux passing through said object, said sensing means being engaged with said first and second magnet means, respectively, for providing a magnetic flux return path having a maximum capacity to return to said first and second magnet means magnetic flux less than or equal to a predetermined maximum allowable magnetic flux deviance generated by a fault in said object, said maximum allowable magnetic flux deviance being less than the saturated magnetic flux capacity of said object.

2. The apparatus of claim 1 further comprising means for positioning said object centrally within said cavities.

3. The apparatus of claim 2 wherein said positioning means comprises a plurality of roller guides extending between said housing and said object.

4. The apparatus of claim 3 wherein said sensing means comprises a magnetic field detector.

5. The apparatus of claim 4 wherein said sensing means comprises one or more Hall effect sensors.

6. The apparatus of claim 5 wherein said Hall effect sensors form a circumferential array.

7. The apparatus of claim 6 wherein said array of said Hall effect sensors is located an equal distance from said first and second magnet means.

8. The apparatus of claim 7 wherein each of said Hall effect sensors is contained within a sensor housing.

9. The apparatus of claim 8 wherein said sensor housing forms said magnetic return path.

10. The apparatus of claim 9 further comprising an adapter demountably secured to said sensor housing.

11. The apparatus of claim 10 further comprising a kit of a plurality of user-mountable adapters.

12. The apparatus of claim 9 further comprising a second sensing means attached to said first magnet means at a theoretical null point thereon.

13. The apparatus of claim 11 wherein second sensing means comprises a Hall effect sensor.

14. A method for magnetically sampling uniformity of an elongate object, comprising the steps of:
   creating a magnetic field between a first magnet means and a second magnet means;
   providing a metallic magnetic flux return path engaged with said first magnet means and said second magnet means, said metallic magnetic flux return path having a maximum capacity to return to said first and second magnet means magnetic flux less than or equal to a predetermined maximum allowable magnetic flux deviance generated by a fault in said object, said maximum allowable magnetic flux deviance being less than the saturated magnetic flux capacity of said object;
   passing said object through said magnetic field for passing magnetic flux through said object;
   sensing variations in said magnetic flux passing through said object; and
   storing said variations in magnetic flux in a memory.

15. The method of claim 14 further comprising the steps of normalizing and digitizing said variations prior to said storage step.

16. The method of claim 14 further comprising the step of processing said variations to determine the integrity of said object.

17. A method for magnetically sampling uniformity of an elongate object, comprising the steps of:
   creating a magnetic field between a first magnet and a second magnet;
   providing a metallic magnetic flux return path engaged with said first magnet and said second magnet, said metallic magnetic flux return path having a maximum capacity to return to said first and second magnets magnetic flux less than or equal to a predetermined maximum allowable magnetic flux deviance generated by a fault in said object, said maximum allowable magnetic flux deviance being less than the saturated magnetic flux capacity of said object;
   passing said object through said magnetic field for passing magnetic flux through said object;
   sensing variations in said magnetic flux passing through said object; and
   processing said variations to determine the integrity of said object.

18. Apparatus, comprising:
   first and second magnet housings each comprising a body with a central cavity;
   a plurality of magnets disposed circumferentially within each of said magnet housings to approximate a cylindrical magnetic coil for passing magnetic flux through an object disposed in said central cavity;
   sensing means for sensing variations in magnetic flux passing through an object disposed in said central cavity and generating corresponding electrical signals, wherein said sensing means is engaged with said first and second magnet housings to provide a magnetic field return path to said magnets, said magnetic field return path having a maximum capacity to return to said magnets magnetic flux less than or equal to the magnetic flux required to saturate an object disposed in said central cavity, said magnetic flux required to saturate an object disposed in said central cavity being less than the magnetic flux created by the plurality of magnets;

means for storing said electrical signals; and means for outputting said stored signals.

19. The apparatus of claim 18 further comprising one or more pairs of diametrically opposed roller guide means connected to each of said magnet housings.

20. The apparatus of claim 18 wherein said storing means are connected to said housings.

21. A method for magnetically sampling uniformity of an elongate object, comprising the steps of:

creating a magnetic field between a first magnet and a second magnet;

providing a metallic magnetic flux return path engaged with said first magnet and said second magnet, said metallic magnetic flux return path having a maximum capacity to return to said first and second magnets magnetic flux less than or equal to a predetermined maximum allowable magnetic flux deviance generated by a fault in said object, said maximum allowable magnetic flux deviance being less than the saturated magnetic flux capacity of said object;

passing said object through said magnetic field for passing magnetic flux through said object;

generating a first set of electrical signals via a first sensing means disposed a predetermined distance from said object which are responsive to said magnetic field passing through said object;

generating a second set of electrical signals via a second sensing means disposed a distance from said object not equal to said predetermined distance which are responsive To said magnetic field passing through said object;

storing said first and second sets of electrical signals in a memory.

22. The method of claim 21 further comprising the step of processing said electrical signals and obtaining output.

23. Apparatus for magnetically testing an elongate object moving relative to said apparatus, comprising:

means for inducing a magnetic field in a portion of said object whereby said magnetic field experiences flux changes according to changes in the condition of said portion, said means for inducing a magnetic field comprising first and second magnet housings and a plurality of permanent magnets spaced circumferentially within each of said magnet housings defining a central cavity for receiving said object, sensing means disposed between said first and second magnet housings for sensing changes in said flux, said sensing means comprising:

a sensor housing defining a central cavity for receiving said object, said sensor housing providing a magnetic flux return path having a maximum capacity to return to said first and second magnet housings magnetic flux less than or equal to a predetermined maximum allowable magnetic flux deviance generated by a fault in said object, said maximum allowable magnetic flux deviance being less than the saturated magnetic flux capacity of said object;

a first array of a plurality of sensing elements supported in said sensor housing equidistant between said first and second magnet housings and arranged circumferentially around said central cavity, said sensing elements being magnetically shielded from said magnetic field by said sensor housing; and a second array of a plurality of sensing elements supported in said sensor housing adjacent to said permanent magnets of said first magnet means, coupled to a theoretical null point thereon, arranged circumferentially around said object, and means for supporting said object for relative movement with respect to said inducing means and said sensing means.

24. Apparatus according to claim 23 further comprising a magnetically-insulating adapter demountably secured to said sensor housing providing an extension thereof.

25. Apparatus for simultaneously sampling uniformity of a plurality of elongate objects, comprising:

a plurality of housings coupled in parallel, each said housing having means for receiving a single elongate object, wherein each housing comprises:

first and second magnet means disposed therein for forming a magnetic field therebetween for passing magnetic flux through said object, said first and second magnet means respectively comprising a plurality of circumferentially disposed magnets approximating a cylindrical magnetic coil having a central cavity for receiving said object, wherein said cavities are longitudinally aligned;

sensing means for sensing variations in said magnetic flux passing through said object, said sensing means being engaged with said first and second magnet means, respectively, for providing a magnetic flux return path having a maximum capacity to return to said first and second magnet means magnetic flux less than or equal to a predetermined maximum allowable magnetic flux deviance generated by a fault in said object, said maximum allowable magnetic flux deviance being less than the saturated magnetic flux capacity of said object; and a plurality of roller guides extending between said housing and said object.

26. The apparatus of claim 25 further comprising mounting means attached to said apparatus.

27. The apparatus of claim 1 wherein said sensing means is magnetically engaged with said first magnet means and said second magnet means.

28. The method of claim 14 wherein said magnetic flux return path is magnetically engaged with said first magnet means and said second magnet means.

29. The method of claim 17 wherein said magnetic flux return path is magnetically engaged with said first magnet and said second magnet.

30. The method of claim 21 wherein said metallic magnetic flux return path is magnetically engaged with said first magnet and said second magnet.

31. The apparatus of claim 30 wherein said sensing means is magnetically engaged with said first magnet means and said second magnet means.

\* \* \* \* \*